US007662615B2

(12) United States Patent
Chang et al.

(10) Patent No.: US 7,662,615 B2
(45) Date of Patent: Feb. 16, 2010

(54) SYSTEM AND METHOD FOR CULTIVATING CELLS

(75) Inventors: Walter Hong-Shong Chang, Jhong-Li (TW); Ming-Tzu Tsai, Jhong-Li (TW)

(73) Assignee: Chung Yuan Christian University, Taoyuan County (TW)

( * ) Notice: Subject to any disclaimer, the term of this patent is extended or adjusted under 35 U.S.C. 154(b) by 1007 days.

(21) Appl. No.: 11/185,749

(22) Filed: Jul. 21, 2005

(65) Prior Publication Data

US 2006/0024822 A1 Feb. 2, 2006

(30) Foreign Application Priority Data

Jul. 27, 2004 (TW) .............................. 93122468 A

(51) Int. Cl.
    *C12M 1/00* (2006.01)
(52) U.S. Cl. ................................................. 435/289.1
(58) Field of Classification Search ............... 435/289.1
    See application file for complete search history.

(56) References Cited

U.S. PATENT DOCUMENTS

| 5,081,036 | A | * | 1/1992 | Familletti | ................ | 435/296.1 |
|-----------|---|---|--------|------------|------------------|-----------|
| 5,143,588 | A | * | 9/1992 | Liboff et al. | ................ | 204/155 |
| 6,001,643 | A | * | 12/1999 | Spaulding | ................ | 435/298.2 |
| 6,326,203 | B1 | * | 12/2001 | Worden et al. | .............. | 435/420 |
| 6,670,169 | B1 | * | 12/2003 | Schob et al. | ............. | 435/286.5 |
| 6,684,106 | B2 | * | 1/2004 | Herbst | .......................... | 607/66 |
| 2004/0005297 | A1 | * | 1/2004 | Connelly et al. | ........... | 424/93.7 |
| 2005/0054101 | A1 | * | 3/2005 | Felder et al. | ................ | 435/383 |

* cited by examiner

*Primary Examiner*—Walter D Griffin
*Assistant Examiner*—Lydia Edwards
(74) *Attorney, Agent, or Firm*—WPAT., P.C.; Justin King

(57) ABSTRACT

The present invention discloses a system for cultivating cells, wherein the system comprises a bioreactor, a pump, and an electromagnetic module comprising a coil and an electromagnetic stimulator. The cells are disposed within the bioreactor. The pump, connected to the bioreactor, is used to drive gas into the bioreactor, so as to ensure a sufficient gas supply for the cells. Additionally, the electromagnetic stimulator, connected to the coil, is used to provide a plurality of first signals, and the first signals are transported to the coil. Then the induced electromagnetic field is produced by the coil, whereby the induced electromagnetic field is applied on the cells within the bioreactor. Moreover, this invention also discloses the method for cultivating cells.

27 Claims, 6 Drawing Sheets

SYSTEM AND METHOD FOR CULTIVATING CELLS

BACKGROUND OF THE INVENTION

1. Field of the Invention

The present invention is generally related to a cell culture system, and more particularly to an in vitro cell culture system comprising bioreactor and electromagnetic stimulator, and the method for cultivating cells.

2. Description of the Prior Art

Electric or mechanical stimulation has been used successfully to treat a wide range of bone disorders, including delayed and onounion fractures, fresh fracture healing, prevention and reverse of osteoporosis, and congenital pseudarthroses. Pulsed electromagnetic fields (PEMF) stimulation has been studied its effects applied on osteoblastic cells growth of rats in vivo (Tsai C. L., Chang W. H., Liu T. K., Wu K. H., Additive effects of prostaglandin E2 and pulsed electromagnetic fields on fracture healing, Chinese Journal of Physiology, 34 (2): 201-11, 1991).

Bioreactor for cell culture has been developed for a long period, wherein the basic principle is to load living cells or tissues into a container with culture medium and gas supply. The bioreactor provides an optimally controlled environment for cell growth (Liao C. J., Chen C. F., Chen J. H., Chiang S. F., Lin Y. J., Chang K. Y., Fabrication of porous biodegradable polymer scaffolds using a solvent merging/particulate leaching method, Journal of Biomedical Materials Research, 59 (4): 676-81, 2002 Mar. 15).

However, PEMF has not been considered as an alternative physical stimulation in bone tissue engineering. Consequently, PEMF might be a more potential perspective and approach applying to three-dimensional culture model in bone tissue engineering.

SUMMARY OF THE INVENTION

In accordance with the present invention, new system and method for cultivating cells in vitro are provided that can meet the requirements of industry, such as: larger scale, easy operation, and low cost.

One object of the present invention is to provide a novel system comprising PEMF stimulator and bioreactor to cultivate cells in vitro.

Another object of this invention is to provide an in vitro cell culture system to regulate cell differentiation and proliferation.

Accordingly, the present invention discloses a system for cultivating cells, wherein the system comprises a bioreactor, a pump, and an electromagnetic module comprising a coil and an electromagnetic stimulator. The cells are disposed within the bioreactor. The pump, connected to the bioreactor, is used to drive gas into the bioreactor, so as to ensure a sufficient gas supply for the cells. Additionally, the electromagnetic stimulator, connected to the coil, is used to provide a plurality of first signals, and the first signals are transported to the coil. Then the induced electromagnetic field is produced by the coil, whereby the induced electromagnetic field is applied on the cells within the bioreactor.

More preferred, the system further comprises scaffolds disposed within the bioreactor, and the cells are located in the scaffolds.

More preferred, the system further comprises a timer, connected to the pump, to cyclically drive gas into the bioreactor.

More preferred, the bioreactor is located inside the coil.

More preferred, the system further comprises a sensor for detecting the electric field intensity of the induced electromagnetic field to generate a plurality of second signals and feedback the second signals to the electromagnetic stimulator, so as to adjust the first signals.

According to results of experiments, PEMF with specific parameters in this provided system not only enhanced osteoblastic differentiation in vitro, but also supplied a suitable condition for osteobalstic growth in this system.

DESCRIPTION OF THE PREFERRED EMBODIMENTS

Figure 1A:
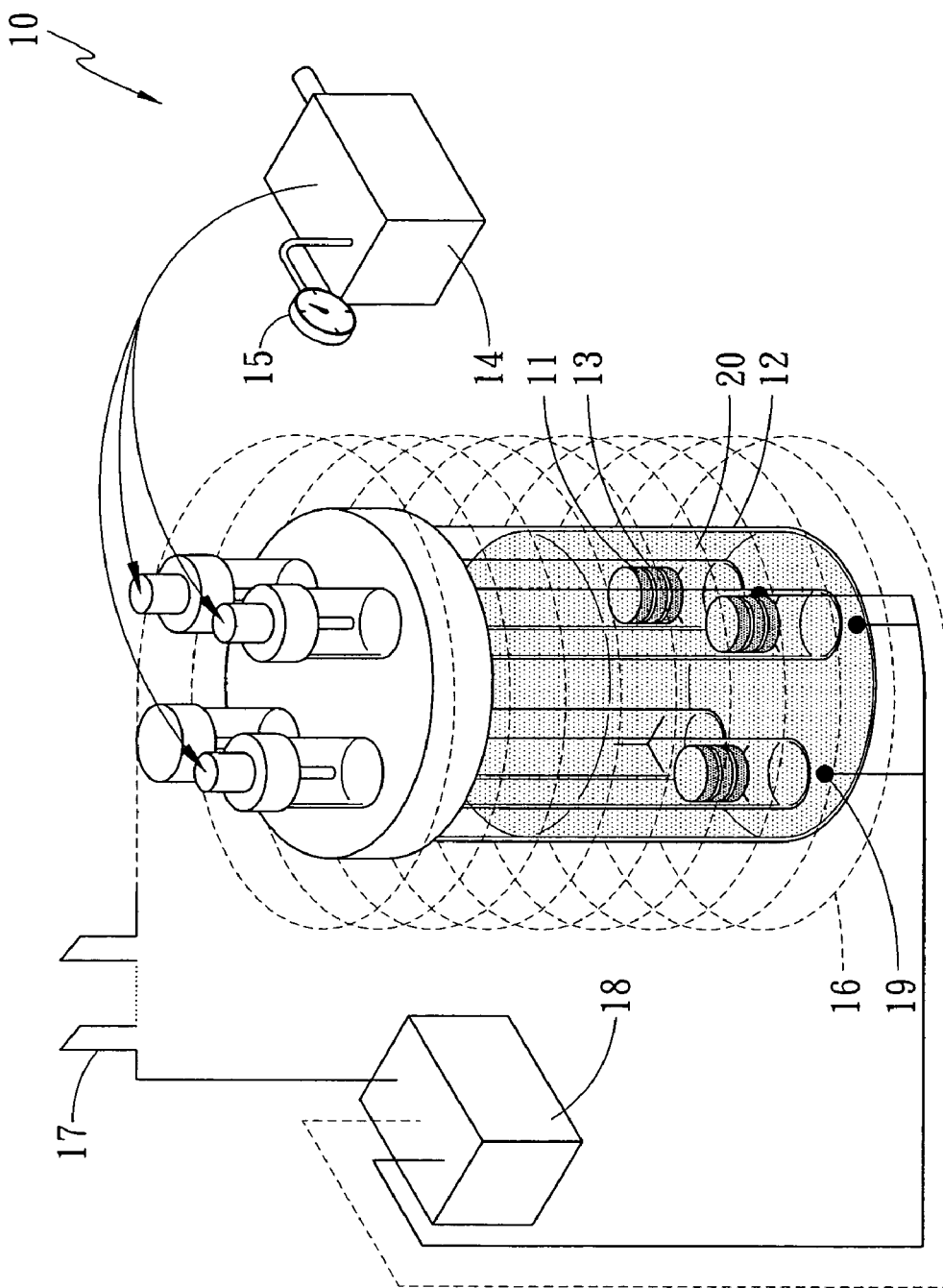
FIG. 1A is a schematic diagram of a system for cultivating cells in vitro, in accordance with the embodiment of the present invention.
Figure 1B:
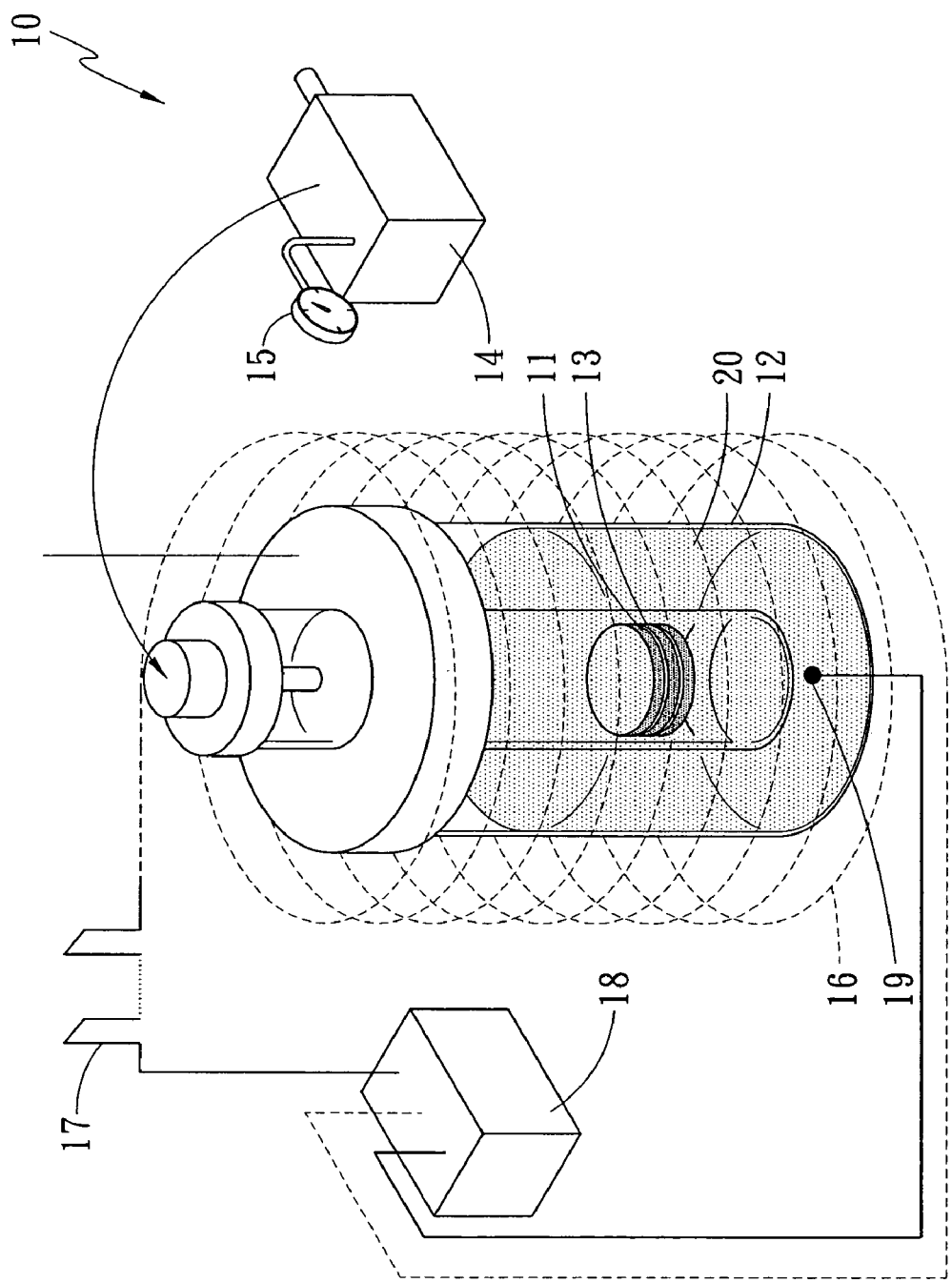
FIG. 1B is a schematic diagram of a system for cultivating cells in vitro, in accordance with the embodiment of the present invention.
Figure 2:
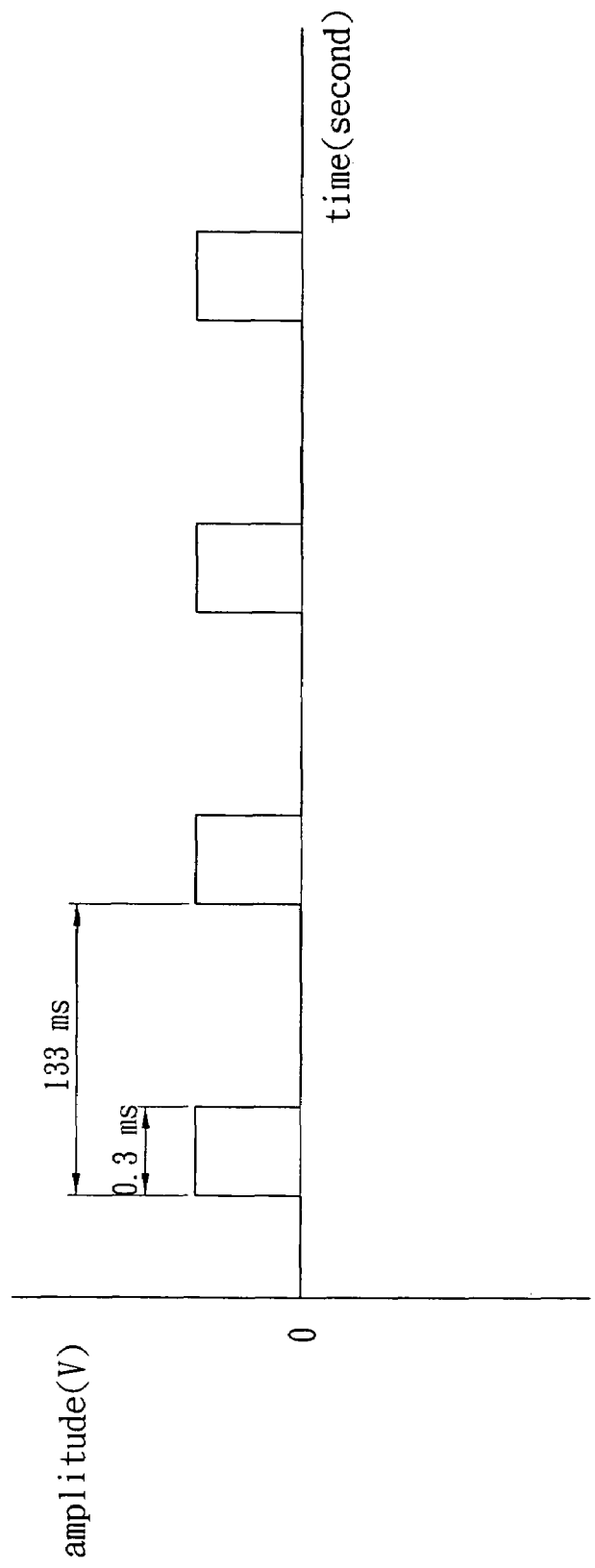
FIG. 2 is a waveform diagram of the first signals provided by the electromagnetic stimulator, in accordance with the embodiment of the present invention.

Referring to FIG. 1 and FIG. 2, in an embodiment of this invention, a system 10 is provided for cultivating cells, especially for osteoblastic cells. The mentioned system 10 comprises a bioreactor 12, a pump 14, and an electromagnetic module comprising a coil 16 and an electromagnetic stimulator 18. The bioreactor 12 is a closed apparatus or container, and the cells 11 and culture medium 20 are located within the bioreactor 12. In a better example of this embodiment, the system 10 further comprises scaffolds 13 disposed within the bioreactor 12, and the cells are located in the scaffolds 13. The scaffolds are three-dimensional and are composed of porous and/or solid fibers of biocompatible, synthetic polymer that are preferably biodegradable. More preferred, the scaffolds are disc-shaped, so as to stake them up coaxially. The pump 14, connected to the bioreactor 12, is used to drive gas into the bioreactor 12, so as to ensure a sufficient gas supply for the cells, wherein oxygen-based gas is preferred. The mentioned system 10 further comprises a timer 15, connected to the pump 14, to cyclically drive gas into the bioreactor 12.

In this embodiment, the coil 16 is used for generating an induced electromagnetic field applied on the cells 11 within the bioreactor 12, wherein the coil 16 comprises spiro coil. In another better example of this embodiment, the bioreactor 12 is located inside the coil 16. The electromagnetic stimulator 18, connected to the coil 16, is used to provide a plurality of first signals 17, and the first signals 17 are transported to the coil 16. Then the induced electromagnetic field is produced by the coil 16, whereby the induced electromagnetic field is applied on the cells 11 within said bioreactor 12. When the mentioned scaffolds are disc-shaped and staked up coaxially, the direction of the magnetic field of the induced electromagnetic field is perpendicular to the scaffolds. Additionally, the electromagnetic stimulator 18 is able to adjust the waveform, frequency, and amplitude of the first signals 17, so as to change the pulse pattern, frequency, and intensity of the induced electromagnetic field, wherein the induced electromagnetic field is also called "stimulation" for the cells 11. In this invention, stimulation with low frequency and low intensity is applied for accelerating osteoblastic cells growth in vitro. Moreover, the system 10 further comprises a sensor 19 for detecting the electric field intensity of the induced electromagnetic field to generate a plurality of second signals and feedback the second signals to the electromagnetic stimulator 18, so as to adjust the first signals 17.

In this embodiment, the type of the first signals 17 can be single pulse or pulse burst. Referring to FIG. 2, in still another better example of this embodiment, the first signals 17 are single pulse, wherein the frequency of the first signals is 7.5 Hz. Therefore, the pulse period of the first signals is 133 ms, and pulse width is 0.3 ms. The electric field intensity of the induced electromagnetic field ranges from 1 to 10 mV/cm.

Experiments and Results

Scaffolds with osteoblastic cells were on the exposure of pulsed electromagnetic field (PEMF) stimulation with specific parameters: single pulsed wave, pulse width of 0.3 ms, extremely low frequency of 7.5 Hz, and induced electric fields intensities of 4 and 8 mV/cm. These matrices were divided into three groups: Control (matrices were not on the exposure of PEMF stimulation), PEMF-2 hr (matrices were on the exposure of PEMF stimulation for 2 hr/day), and PEMF-8 hr (matrices were on the exposure of PEMF stimulation for 8 hr/day). Each group was cultured in the mentioned system for 2 weeks. Culture medium and matrices of three groups were retrieved at each week for biochemical and histomorphological assays.

Figure 3A:
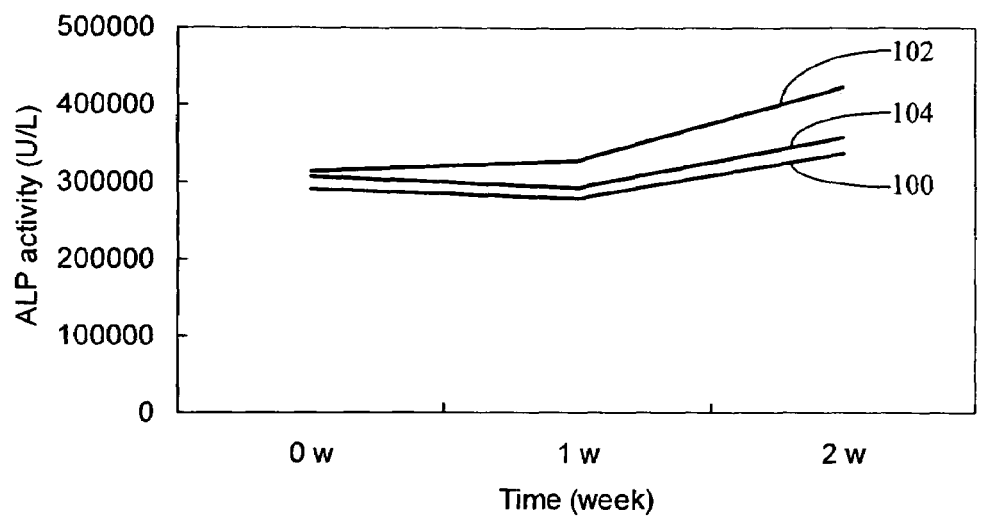
FIG. 3A shows the changes of alkaline phosphatase concentrations of in culture medium under PEMF stimulation with the induced electric field intensity of 4 mV/cm, in accordance with the Experiments and Results of the present invention.
Figure 3B:
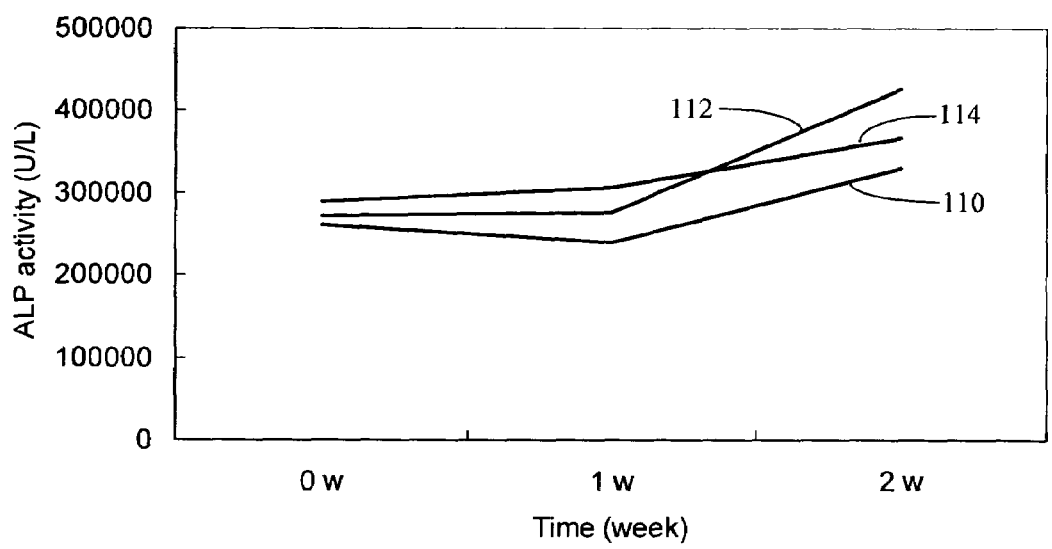
FIG. 3B shows the changes of alkaline phosphatase concentrations of in culture medium under PEMF stimulation with the induced electric field intensity of 8 mV/cm, in accordance with the Experiments and Results of the present invention.

FIG. 3A shows the changes of alkaline phosphatase concentrations (ALP activities) of in culture medium under PEMF stimulation with the induced electric field intensity of 4 mV/cm. Curves 100, 102, and 104 respectively represent groups Control, PEMF-2 hr, and PEMF-8 hr. According to FIG. 3A, the ALP activities of groups PEMF-2 hr and PEMF-8 hr increased significantly with time increased, wherein group PEMF-2 hr expressed the highest ALP activities. Since ALP is an early marker of osteoblastic differentiation, the treatment by PEMF of osteoblastic cells may accelerate cellular mineralization, especially for group PEMF-2 hr. On the other hand, FIG. 3B shows the changes of ALP activities of in culture medium under PEMF stimulation with the induced electric fields intensity of 8 mV/cm. Curves 110, 112, and 114 respectively represent groups Control, PEMF-2 hr, and PEMF-8 hr. Similar to FIG. 3A, the ALP activities of groups PEMF-2 hr and PEMF-8 hr increased significantly with time increased, wherein group PEMF-2 hr expressed the highest ALP activities. Comparing FIG. 3A with FIG. 3B, under PEMF stimulation with different induced electric field intensity, group PEMF-2 hr showed the best performance for cellular differentiation within 2 weeks.

Figure 4A:
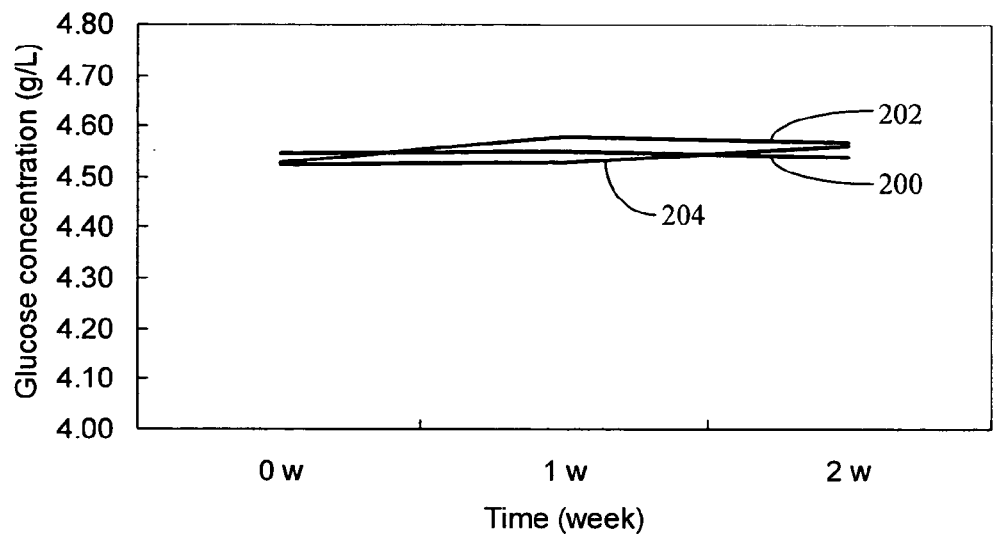
FIG. 4A shows the changes of glucose concentrations of in culture medium under PEMF stimulation with the induced electric field intensity of 4 mV/cm, in accordance with the Experiments and Results of the present invention.
Figure 4B:
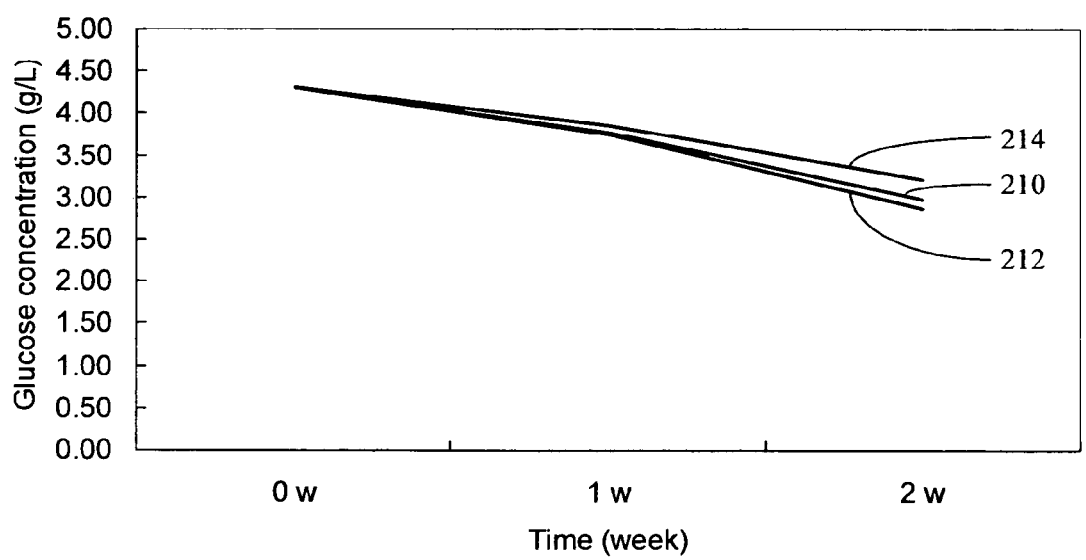
FIG. 4B shows the changes of glucose concentrations of in culture medium under PEMF stimulation with the induced electric field intensity of 8 mV/cm, in accordance with the Experiments and Results of the present invention.

FIG. 4A shows the changes of glucose concentrations of in culture medium under PEMF stimulation with the induced electric field intensity of 4 mV/cm. Curves 200, 202, and 204 respectively represent groups Control, PEMF-2 hr, and PEMF-8 hr. According to FIG. 4A, the tendencies of glucose levels of three groups were similar, wherein group PEMF-8 hr expressed the lowest glucose level at the 1st week, which meant group PEMF-8 hr needed more energy by consuming more glucose. On the other hand, FIG. 4B shows the changes of glucose concentrations of in culture medium under PEMF stimulation with the induced electric field intensity of 8 mV/cm. Curves 210, 212, and 214 respectively represent groups Control, PEMF-2 hr, and PEMF-8 hr. According to FIG. 4B, the tendencies of glucose levels of groups PEMF-2 hr and PEMF-8 hr decreased similarly, wherein group PEMF-2 hr expressed the lowest glucose level at the 2nd week, which meant group PEMF-2 hr needed more energy by consuming more glucose. Comparing FIG. 4A with FIG. 4B, the glucose level of curves 212 and 214 are lower than curves 202 and 204. Therefore, under PEMF stimulation with higher induced electric field intensity, osteoblastic cells needed more energy by consuming more glucose with time increased. This result also implied that PEMF stimulation accelerated osteoblastic cells' differentiation.

Figure 5A:
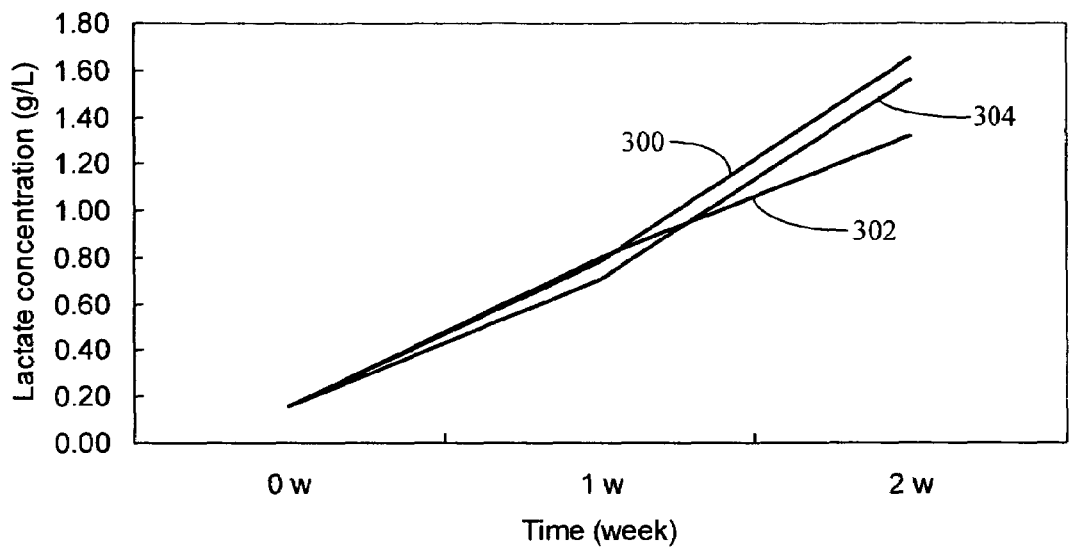
FIG. 5A shows the changes of lactate concentrations of in culture medium under PEMF stimulation with the induced electric field intensity of 4 mV/cm, in accordance with the Experiments and Results of the present invention.
Figure 5B:
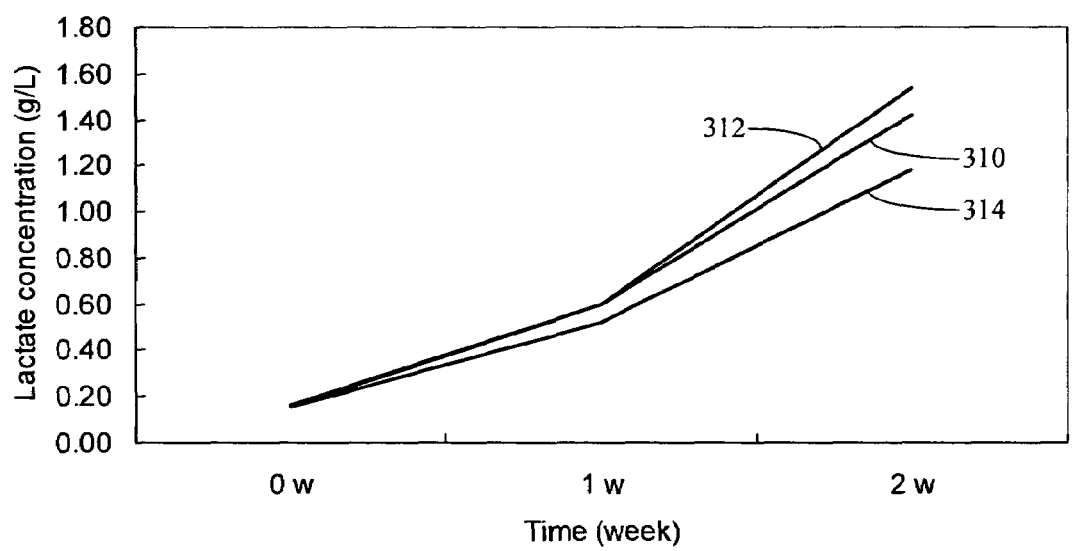
FIG. 5B shows the changes of lactate concentrations of in culture medium under PEMF stimulation with the induced electric field intensity of 8 mV/cm, in accordance with the Experiments and Results of the present invention.

FIG. 5A shows the changes of lactate concentrations of in culture medium under PEMF stimulation with the induced electric field intensity of 4 mV/cm. Curves 300, 302, and 304 respectively represent groups Control, PEMF-2 hr, and PEMF-8 hr. On the other hand, FIG. 5B shows the changes of lactate concentrations of in culture medium under PEMF stimulation with the induced electric fields intensity of 8 mV/cm. Curves 310, 312, and 314 respectively represent groups Control, PEMF-2 hr, and PEMF-8 hr. According to FIGS. 5A and 5B, lactate concentrations all increased at each time point. The results revealed that the metabolism of osteoblastic cells cultured in scaffolds disposed within the bioreactors under PEMF stimulation were stable and it indicated that cells were able to and suitable to live and grow in this provided system.

To sum up, the present invention discloses a novel system comprising PEMF stimulator and bioreactor, and the effect of PEMF was proved in bone tissue engineering in an osteoblastic culture model. PEMF with specific parameters in this provided system not only enhanced osteoblastic differentiation in vitro, but also supplied a suitable condition for osteobalstic growth in this system.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:
1. A system for cultivating cells, comprising:
a bioreactor, wherein the cells are disposed within said bioreactor, further comprising a plurality of scaffolds disposed within said bioreactor, and the cells are located in said plurality of scaffolds, wherein said plurality of scaffolds are disc-shaped and said plurality of scaffolds are staked up coaxially;

a pump connected to said bioreactor, wherein said pump is used to drive gas into said bioreactor;

a coil for generating an induced electromagnetic field applied on the cells within said bioreactor; and an electromagnetic stimulator connected to said coil, wherein said electromagnetic stimulator is used to provide a plurality of first signals and produce said induced electromagnetic field by said coil, whereby said induced electromagnetic field is applied on the cells within said bioreactor, wherein the direction of the magnetic field of said induced electromagnetic field is perpendicular to said plurality of scaffolds.

2. The system according to claim 1, wherein the cells are osteoblastic cells.

3. The system according to claim 1, wherein the gas is oxygen-based.

4. The system according to claim 1, further comprising a timer connected to said pump, so as to cyclically drive gas into said bioreactor.

5. The system according to claim 1, wherein said coil is spiro coil.

6. The system according to claim 1, wherein said bioreactor is located inside said coil.

7. The system according to claim 1, wherein the frequency of said plurality of first signals is 7.5 Hz.

8. The system according to claim 1, wherein the type of said plurality of first signals is single pulse.

9. The system according to claim 8, wherein the pulse period is 133 ms, and pulse width is 0.3 ms.

10. The system according to claim 1, wherein the type of said plurality of first signals is pulse burst.

11. The system according to claim 1, wherein the electric field intensity of said induced electromagnetic field ranges from 1 to 10 mV/cm.

12. The system according to claim 1, wherein said plurality of first signals are provided equivalent to or less than 8 hours per day.

13. The system according to claim 1, further comprising a sensor for detecting the electric field intensity of said induced electromagnetic field to generate a plurality of second signals and feedback said plurality of second signals to said electromagnetic stimulator, so as to adjust said plurality of first signals.

14. A method for cultivating cells, comprising:

loading the cells into a bioreactor, wherein the cells are disposed within said bioreactor, wherein the cells are located in a plurality of scaffolds disposed within said bioreactor, wherein said plurality of scaffolds are disc-shaped and said plurality of scaffolds are staked coaxially;

driving gas into said bioreactor by a pump connected to said bioreactor; and generating a electromagnetic field by a electromagnetic module, wherein said induced electromagnetic field is applied on the cells within said bioreactor, wherein the direction of the magnetic field of said induced electromagnetic field is perpendicular to said plurality of scaffolds.

15. The method according to claim 14, wherein the cells are osteoblastic cells.

16. The method according to claim 14, wherein the gas is oxygen-based.

17. The method according to claim 14, wherein the gas is cyclically driven into said bioreactor by a timer connected to said pump.

18. The method according to claim 14, wherein said coil is spiro coil.

19. The method according to claim 14, wherein said bioreactor is located inside said coil.

20. The method according to claim 14, wherein the electric field intensity of said induced electromagnetic field ranges from 1 to 10 mV/cm.

21. The method according to claim 14, wherein said electromagnetic module comprises:

a coil; and an electromagnetic stimulator connected to said coil, wherein said electromagnetic stimulator is used to provide a plurality of first signals and produce said induced electromagnetic field by said coil.

22. The method according to claim 21, wherein the frequency of said plurality of first signals is 7.5 Hz.

23. The method according to claim 21, wherein the type of said plurality of first signals is single pulse.

24. The method according to claim 23, wherein the pulse period is 133 ms, and pulse width is 0.3 ms.

25. The method according to claim 21, wherein the type of said plurality of first signals is pulse burst.

26. The method according to claim 21, wherein said plurality of first signals are provided equivalent to or less than 8 hours per day.

27. The method according to claim 21, further comprising a feedback process which comprises:

detecting the electric field intensity of said induced electromagnetic field by a sensor, and generating a plurality of second signals; and feed backing said plurality of second signals to said electromagnetic stimulator, so as to adjust said plurality of first signals.

* * * * *